(12) United States Patent
Turner

(10) Patent No.: US 10,391,517 B1
(45) Date of Patent: Aug. 27, 2019

(54) DISPENSER ASSEMBLY

(71) Applicant: Sulzer Mixpac AG, Haag (CH)

(72) Inventor: Hayden Turner, Ayer, MA (US)

(73) Assignee: SULZER MIXPAC AG, Haag (CH)

( * ) Notice: Subject to any disclaimer, the term of this patent is extended or adjusted under 35 U.S.C. 154(b) by 0 days.

(21) Appl. No.: 15/992,666

(22) Filed: May 30, 2018

(51) Int. Cl.
  *B05C 17/01* (2006.01)
  *B05C 17/005* (2006.01)
  *A61C 9/00* (2006.01)

(52) U.S. Cl.
  CPC ........ *B05C 17/0123* (2013.01); *A61C 9/0026* (2013.01); *B05C 17/00566* (2013.01); *B05C 17/00596* (2013.01)

(58) Field of Classification Search
  CPC .......... B05C 17/0123; B05C 17/00566; B05C 17/00596; A61C 9/0026
  USPC .... 222/145.6, 391, 192, 325–327, 137, 386; 269/3, 6, 246
  See application file for complete search history.

(56) References Cited

U.S. PATENT DOCUMENTS

| | | | |
|---|---|---|---|
| 3,458,090 A | 7/1969 | Scoggin, Jr. | |
| 5,549,225 A * | 8/1996 | Lii | B05C 17/01 222/192 |
| 5,562,623 A | 10/1996 | Shonfeld et al. | |
| 5,593,066 A * | 1/1997 | Konuma | B05C 17/00506 222/105 |
| 5,788,126 A | 8/1998 | Chang | |
| 6,382,466 B1 * | 5/2002 | Schneider | B05C 17/00553 222/137 |
| 6,752,782 B2 | 6/2004 | Liao | |
| 8,123,085 B2 * | 2/2012 | Shih | B05C 17/01 222/192 |

* cited by examiner

*Primary Examiner* — Lien M Ngo
(74) *Attorney, Agent, or Firm* — Global IP Counselors, LLP

(57) ABSTRACT

A dispenser assembly includes a rod, a plunger and a stopper. The rod has a plunger receiving end with a clip receiving recess. The plunger has a rod receiving structure with a rod engaging clip biased to fit to the clip receiving recess of the rod for movement therewith. The stopper has a plunger receiving space that defines an aperture extending through the plunger receiving space with the rod extending through the aperture. The plunger receiving space is dimensioned such that with the rod receiving structure of the plunger located within the plunger receiving space, movement of the rod engaging clip is restricted by contact with surfaces of the plunger receiving space preventing release of the rod from the plunger.

19 Claims, 15 Drawing Sheets

DISPENSER ASSEMBLY

BACKGROUND

Field of the Invention

The present invention generally relates to a dispenser assembly. More specifically, the present invention relates to dispenser assembly that includes a stopper, a plunger and a rod, where the rod is releasable from the plunger when spaced apart from the stopper, and the plunger prevents the release of the rod with a portion of the plunger moved into a cylindrically shaped space within the stopper.

Background Information

In various industries, such as the construction and dental sectors, cartridges are frequently used to dispense liquids, for example, sealing components, components for chemical dowels or chemical anchors, adhesives, pastes or impression materials in the dental sector.

Conventional dispensers can be single-component systems in which the material to be dispensed is formed from one component and two-component or multicomponent systems in which at least two different components are stored in separate chambers of the same cartridge or in separate cartridges. The two-component or multicomponent systems, the components are mixed by a dynamic or static mixing apparatus. Examples of multicomponent systems include adhesives or chemical dowels which only harden after the mixing of the two components. Two-component systems can also be used in the industrial sector for paints which are often used to generate functional protective layers such as for corrosion protection.

Many conventional systems can include prefilled cartridges designed for a single use. Some prefilled cartridges include an internal piston that is pushed by a plunger of a force applying mechanism within the dispenser to dispense the contents of the cartridge. Some prefilled cartridges do not include a piston and rely on a re-usable piston provided with the dispenser to dispense the contents of the cartridge.

SUMMARY

One object of the present disclosure is to provide a dispenser assembly with a plunger and rod that can be separated from one another only when the plunger is spaced apart from a stopper member of the dispenser assembly.

In view of the state of the known technology, one aspect of the present disclosure is to provide a dispenser assembly with a rod, a plunger and a stopper. The rod has a plunger receiving end with a clip receiving portion. The plunger has a rod receiving structure with a rod engaging clip biased to fit into the clip receiving portion of the rod for movement therewith. The stopper has a plunger receiving space that defines an aperture extending through the plunger receiving space with the rod extending through the aperture. The plunger receiving space is dimensioned such that with the rod receiving structure of the plunger located within the plunger receiving space, movement of the rod engaging clip is restricted by contact with surfaces of the plunger receiving space preventing release of the rod from the plunger.

BRIEF DESCRIPTION OF THE DRAWINGS

Referring now to the attached drawings which form a part of this original disclosure.

DETAILED DESCRIPTION OF EMBODIMENTS

Selected embodiments will now be explained with reference to the drawings. It will be apparent to those skilled in the art from this disclosure that the following descriptions of the embodiments are provided for illustration only and not for the purpose of limiting the invention as defined by the appended claims and their equivalents.

Figure 1:
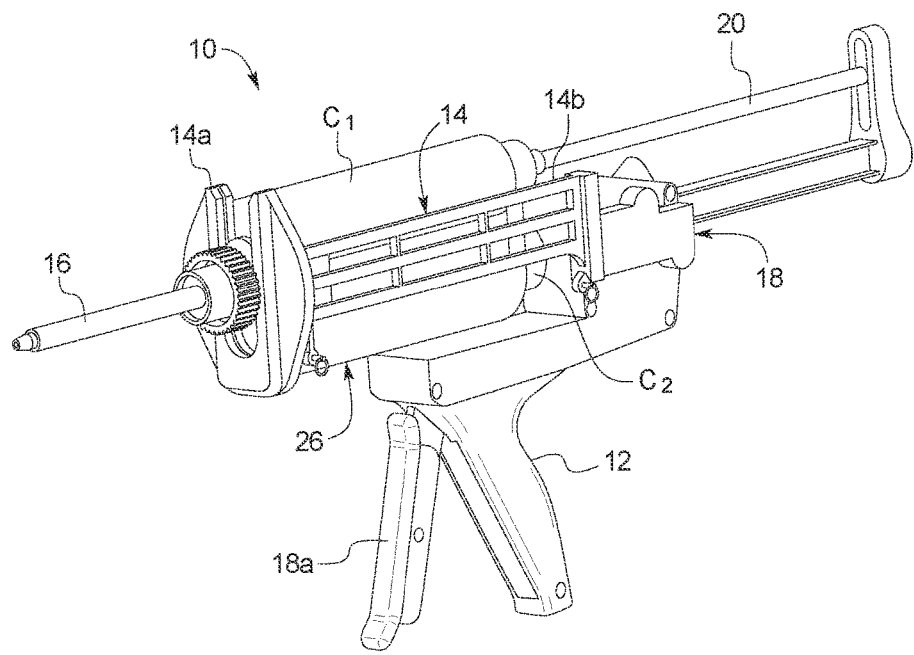
FIG. 1 is a perspective view of a dispenser assembly that includes a force applying rod that has a plunger attached thereto, and a stopper in accordance with a first embodiment.

Referring initially to FIG. 1, a dispenser assembly 10 is illustrated in accordance with a first embodiment. The dispenser assembly 10 includes a handle assembly 12 that has a cartridge receiving structure 14, a dispensing nozzle 16 and a dispensing mechanism 18. The dispenser assembly 10 also includes a rod 20, and, as shown removed from the dispenser assembly 10 in FIG. 2, a plunger 22 and a stopper 24 that co-operate with the rod 20.

The handle assembly 12 includes a trigger 18a that operates the dispensing mechanism 18. The cartridge receiving structure 14 includes a material dispensing end 14a and a stopper supporting end 14b.

The cartridge receiving structure 14 is configured to receive a replaceable cartridge $C_1$ in a conventional manner. The dispenser assembly 10 can be configured to dispense only the contents of the cartridge $C_1$, or as shown the embodiment depicted in FIG. 1, can be configured to dispense the contents of the cartridge $C_1$ and the contents of a second cartridge $C_2$ out of the nozzle 16. An optional mixing chamber (a mixing portion), not shown, can be provided within the nozzle 16 to mix the contents of the cartridge $C_1$ and the contents of the second cartridge $C_2$ as the contents are dispensed.

The handle assembly 12 includes a second cartridge receiving structure 26 that extends parallel to the cartridge receiving structure 14. The second cartridge receiving structure 26 is configured to receive the second cartridge $C_2$. The second cartridge receiving structure 26 can include a second rod (not shown), a second plunger (not shown) and a second stopper (not shown). The second rod has features identical to the features of the rod 20, the second plunger has features identical to the features of the plunger 22, and the second stopper has all the features of the stopper 24. Therefore, for the sake of brevity, only the rod 20, the plunger 22 and the stopper 24 are described herein below. In other words, description of the rod 20 applies equally to the second rod (not shown), description of the plunger 22 applies equally to the second plunger (not shown), and description of the stopper 24 applies to the second stopper (not shown).

Dispensing of the contents of the cartridges $C_1$ and $C_2$ is controlled via operation of the dispensing mechanism 18, which moves the rod 20. In other words, the dispensing mechanism 18 is a rod advancing mechanism that control movement of the rod 20. Movement of the rod 20 causes pressure to be applied to the contents of the cartridge $C_1$, (and the contents of the cartridge $C_2$) in a conventional manner. Since dispensing mechanisms, such as the dispensing mechanism 18 are conventional mechanisms, further description is omitted for the sake of brevity.

Figure 2:
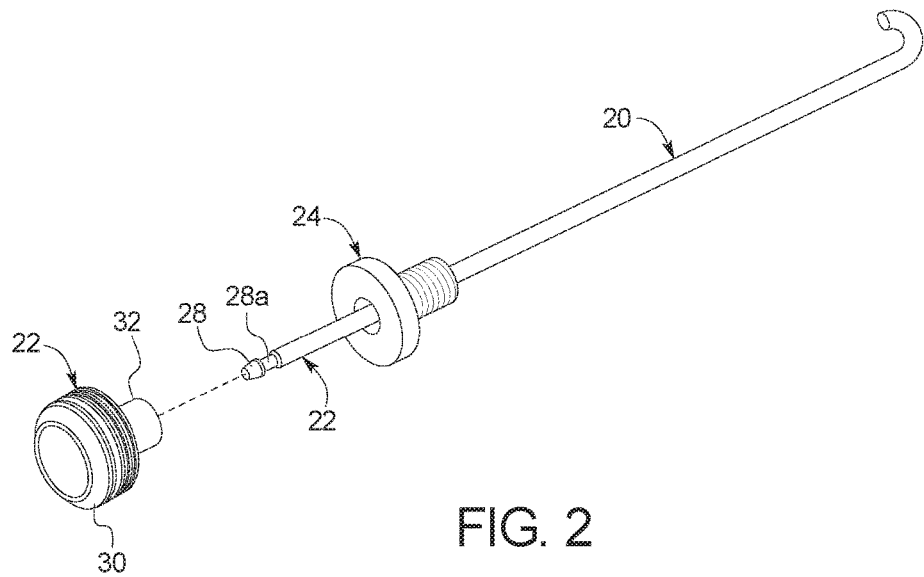
FIG. 2 is an exploded perspective view of the force applying rod, the plunger and the stopper in accordance with a first embodiment.
Figure 3:
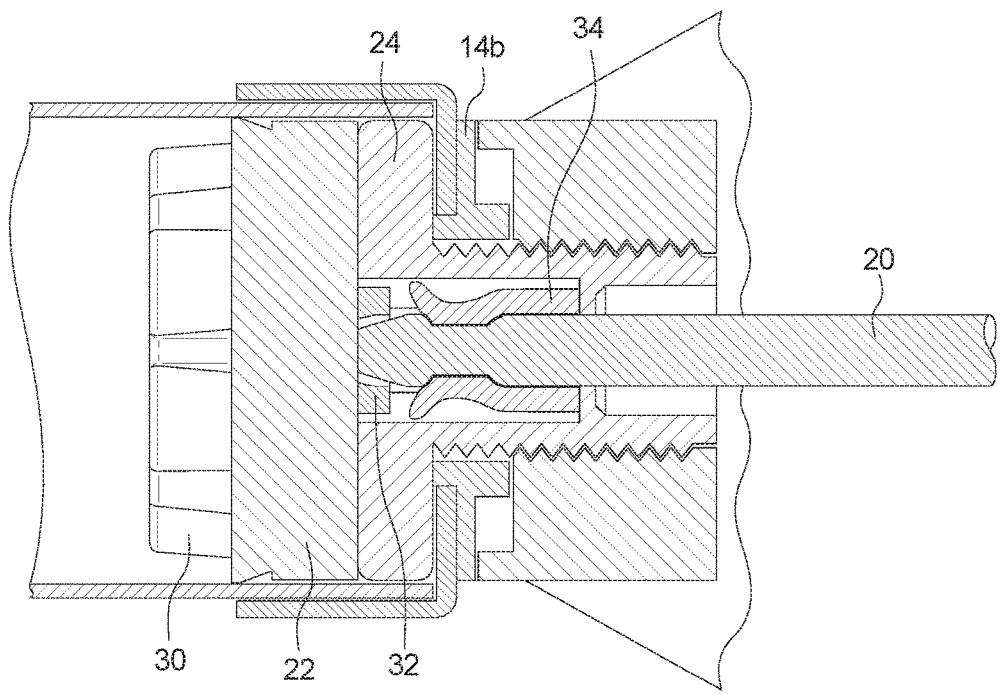
FIG. 3 is a cross-sectional side view of a stopper supporting end of the dispenser assembly showing details of the rod, the plunger and the stopper in accordance with the first embodiment.

As shown removed from the dispenser assembly 10 in FIG. 2, the rod 20 is an elongated member that extends through the stopper 24 and attaches to the plunger 22, as is described in greater detail below.

Descriptions of the rod 20, the plunger 22 and the stopper 24 are now provided with specific reference to FIGS. 3-18. As shown in FIGS. 3-9, the rod 20 has a plunger receiving end 28 that includes a clip receiving recess 28a (also referred to as a clip receiving portion). The clip receiving recess 28a can be an in particular annular recess that defines an outer diameter $D_1$ that is smaller than the overall outer diameter $D_2$ of remainder of the rod 20. Alternatively, the clip receiving recess 28a can be a pair of arcuate recesses that are separated from one another. The arcuate recesses can have, for example, an arcuate length of 90 degrees. In another alternative configuration, the clip receiving recess 28a can be a pair or pairs of rectangular shaped recesses dimensioned to receive rod engaging clips 38 (described in greater detail below). The number of clip receiving recesses can correspond to the number of rod engaging clips 38.

It should be understood from the drawings and the description herein that the dispenser assembly 10 is just one type of dispenser assembly and that the plunger 22 and stopper 24 can be used with any of a variety of dispensing assemblies and is not limited to usage with the dispenser assembly 10 of the first embodiment.

As shown in FIGS. 3-9, the plunger 22 has a disk-shaped portion 30 and a rod receiving structure 32 that are molded together as a single, monolithic unitary element. In the first embodiment shown in FIGS. 3-18, the disk-shaped portion 30 defines a piston that can be inserted into the cartridge $C_1$ in a conventional manner for urging the contents of the cartridge $C_1$ out of the nozzle 16. One such usage of the plunger 22 (piston) with a cartridge is disclosed and further described U.S. patent application Ser. No. 15/855,357, filed Dec. 27, 2017. The drawings and disclosure of U.S. patent application Ser. No. 15/855,357 is incorporated herein by reference in its entirety.

Figure 4:
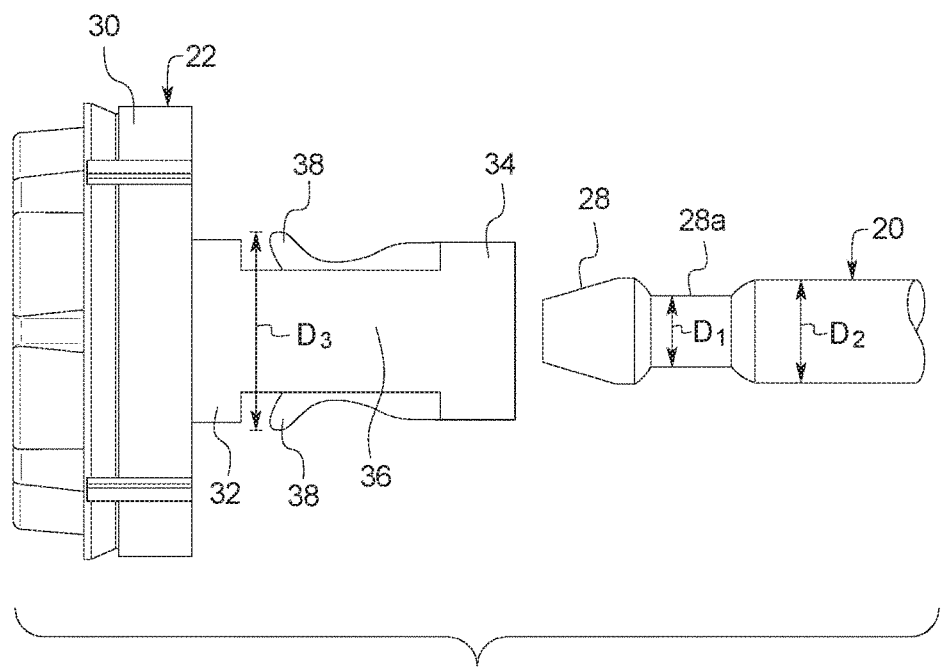
FIG. 4 is an exploded side view of the rod and the plunger shown removed from the stopper and the stopper supporting end of the dispenser assembly in accordance with the first embodiment.
Figure 5:
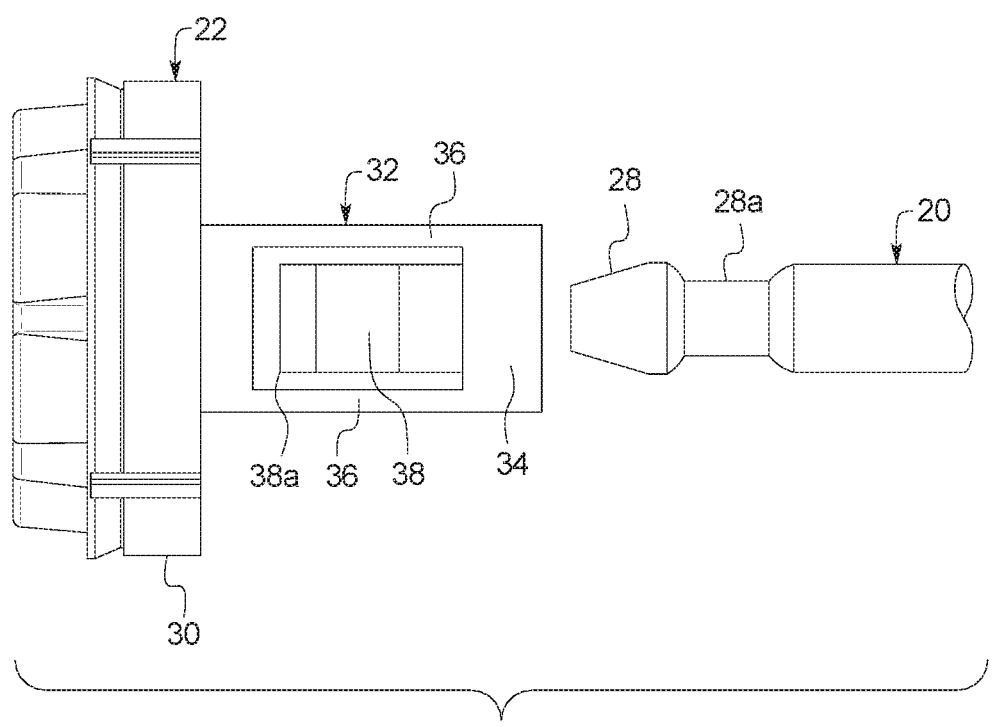
FIG. 5 is another exploded side view of the rod and the plunger with the rod and the plunger rotated 90 degrees relative to their orientation in FIG. 4, in accordance with the first embodiment.
Figure 9:
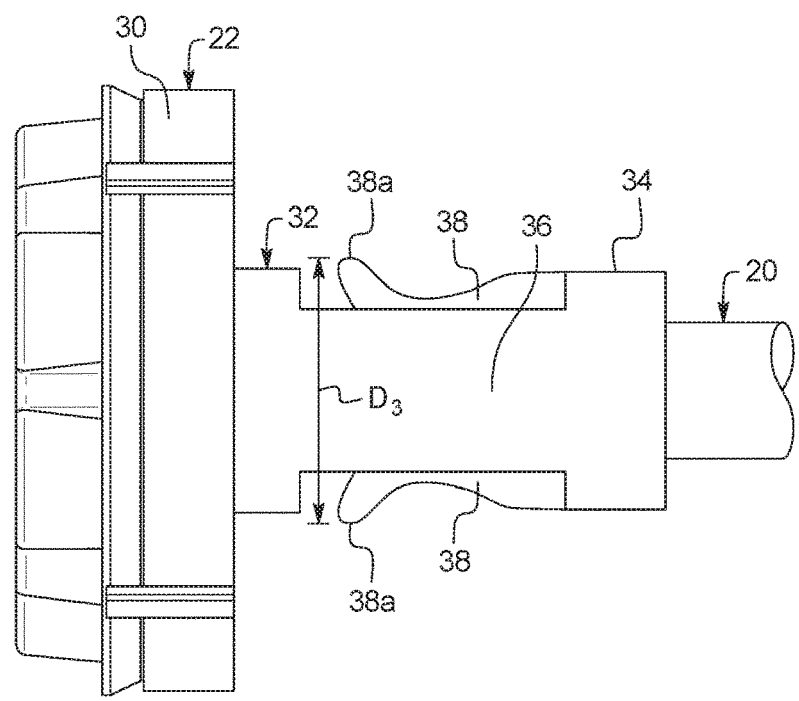
FIG. 9 is a side view of the rod and the plunger showing the rod fully inserted into the plunger with the two biased rod engaging clips contacting the recess formed on the rod, retaining the plunger on the rod in accordance with the first embodiment.

As shown in FIGS. 4-5 and 9, the rod receiving structure 32 is a cylindrically shaped structure that includes an annular end ring 34, support portions 36 and the rod engaging clips 38 (mentioned above).

The support portions 36 extend from the disk-shaped portion 30 to the annular end ring 34. The support portions 36 are basically rigid sections that support the annular end ring 34 and the rod engaging clips 38. In the depicted embodiment there are two support sections 36, with the rod engaging clips 38 being disposed between the support sections 36. Alternatively, three or four rod engaging clips 38 can be provided as part of the rod receiving structure 32 with a corresponding number of support portions 36. The rod engaging clips 38 have free ends 38a. The free ends 38a of the rod engaging clips 38 define an outer diameter $D_3$. Basically, the rod engaging clips 38 are cantilever members that extend from the annular end ring 34 back toward the disk-shaped portion 30. The rod engaging clips 38 are configured and dimensioned to undergo limited elastic deformation relative to the annular end ring 34. In other words, the rod engaging clips 38 can elastically bend in response to a predetermined level of force in an area adjacent to the annular end ring 34. However, upon release of the predetermined level of force, the rod engaging clips 38 return to their original orientation shown in FIGS. 6, 8 and 9.

Figure 6:
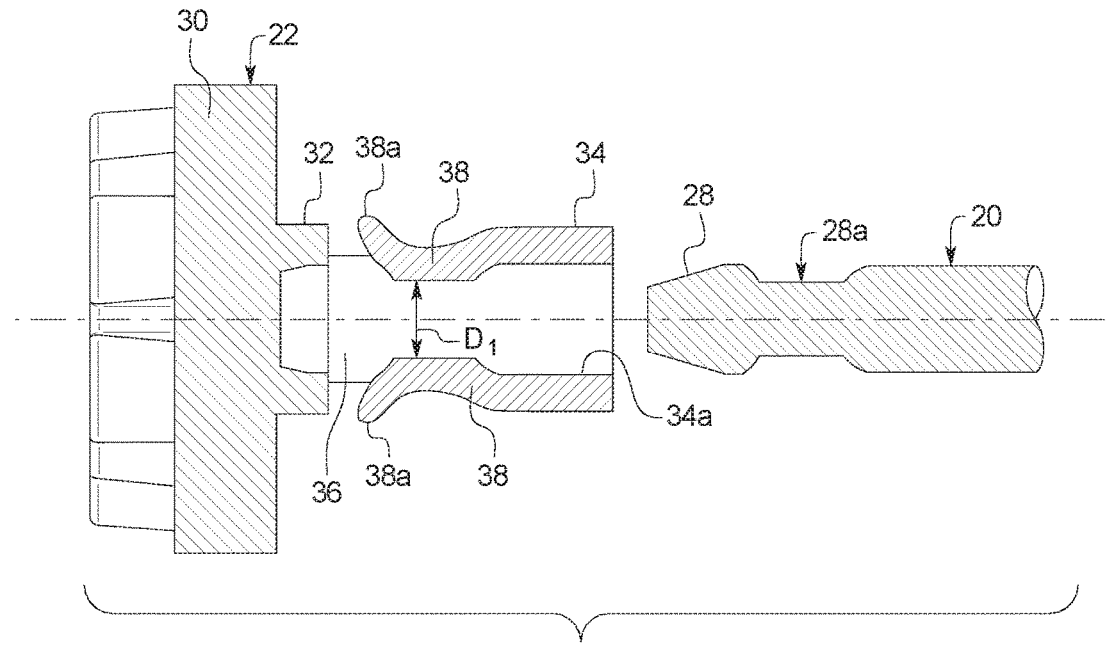
FIG. 6 is an exploded side cross-sectional view of the rod and the plunger shown just prior to attachment of the rod to the plunger in accordance with the first embodiment.
Figure 7:
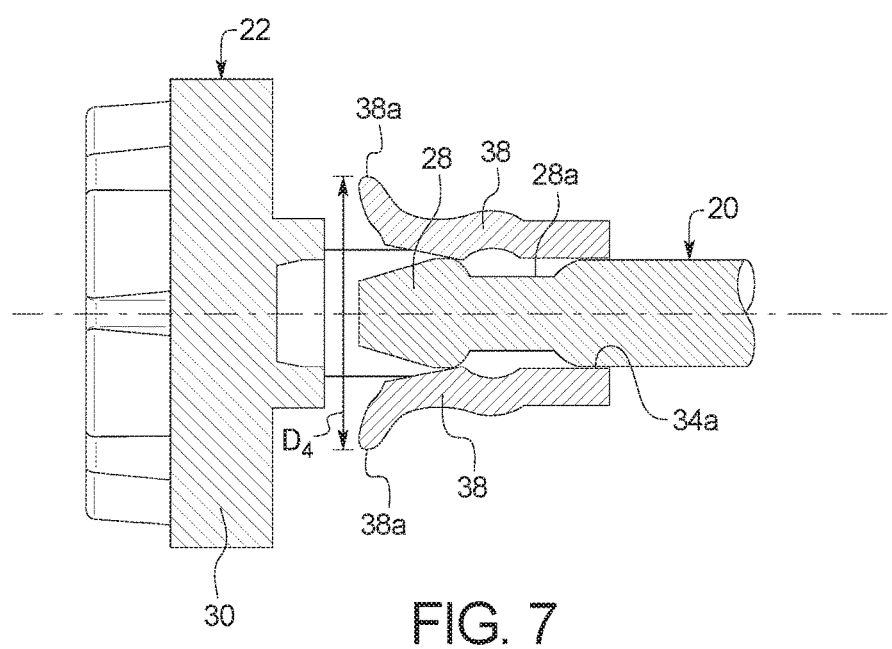
FIG. 7 is a side cross-sectional view of the rod and the plunger similar to FIG. 6 showing the rod partially inserted into the plunger elastically deforming two biased rod engaging clips in accordance with the first embodiment.
Figure 8:
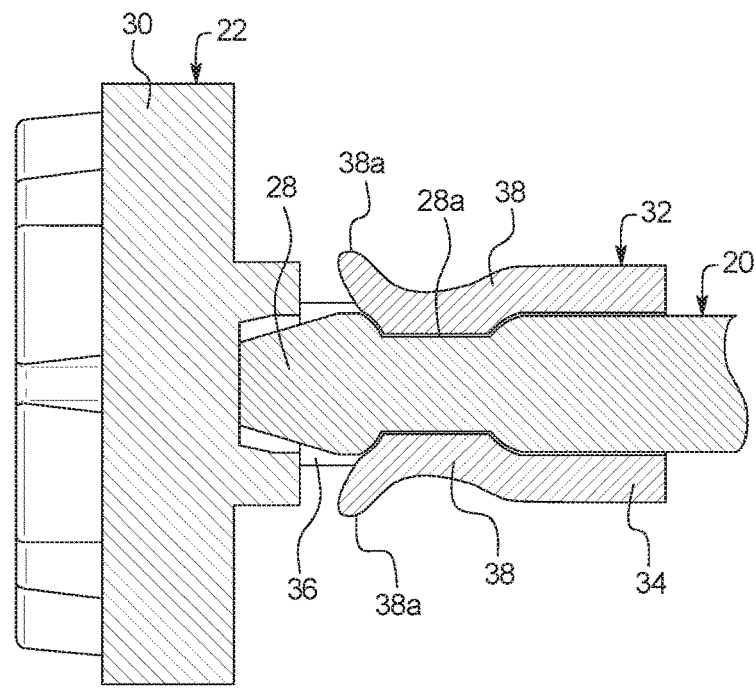
FIG. 8 is another side cross-sectional view of the rod and the plunger similar to FIGS. 6 and 7 showing the rod fully inserted into the plunger with the two rod engaging clips contacting a recess formed on the rod, retaining the plunger on the rod in accordance with the first embodiment.

The disk-shaped portion 30, support portions 36, the rod engaging clips 38 and the annular end ring 34 are formed together as single, unitarily, monolithic member. As shown in FIGS. 6, 7 and 8, the annular end ring 34 defines an opening 34a leads to a central bore that extends from the end of the annular end ring 34, through the annular end ring 34, between the rod engaging clips 38 and to the disk-shaped portion 30.

The plunger 22 is made of a flexible and resilient material such as a plastic or polymer material. The shape, material properties of the material used to manufacture the plunger 22 provide the rod engaging clips 38 with a predetermined level of biasing such that the rod engaging clips 38 are biased into the orientations (positions) shown in FIGS. 3, 4, 6 and 8-11. Consequently, the resilient properties of the rod engaging clips 38 biases them to move toward one another allowing for simple attachment of the rod 20 to the plunger 22, as shown in a sequence of cross-sections images shown in FIGS. 6, 7 and 8. In FIG. 6, the rod 20 is moved toward the opening 34a in the plunger 22. As shown in FIG. 7, as the rod 20 is pushed past the rod engaging clips 38, the rod engaging clips 38 elastically deform to make space for the rod 20. As shown in FIG. 7, with the rod engaging clips 38 being moved radially outward, the free ends 38a of the rod engaging clips 38 define an outer diameter $D_4$, that is larger than the diameter $D_3$. As shown in FIGS. 8 and 9, once the rod 22 has moved fully into the rod receiving structure 32, the rod engaging clips 38 are resiliently restored to their original orientation. In other words, FIGS. 8 and 9 show the rod engaging clips 38 biased to fit to or within the clip receiving recess 28a of the rod 20.

In the depicted first embodiment, the plunger 22 includes two rod engaging clips 28 and two support portions 36 attached to the annular end ring 34. However, it should be understood from the drawings and the description herein that the plunger 22 can be provided with only one rod engaging clip 28, or alternatively 3, 4 or 5 rod engaging clip 28 circumferentially spaced apart from one another with corresponding support portions 36 between adjacent pairs of rod engaging clips.

Figure 10:
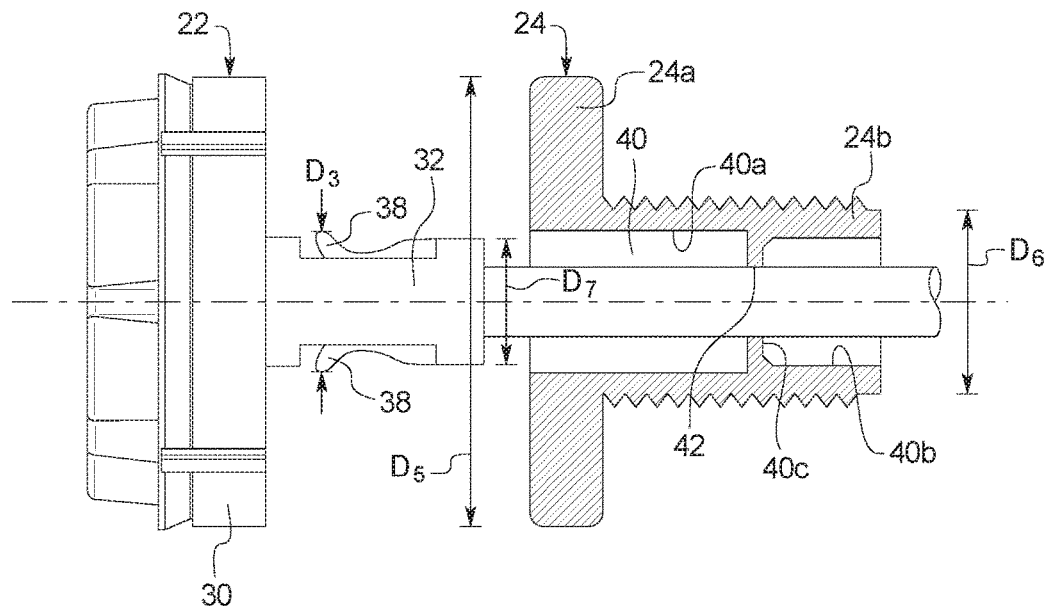
FIG. 10 is a side view of the stopper, the rod and the plunger showing the rod and the plunger fixed to one another, with the plunger spaced apart from the stopper in accordance with the first embodiment.
Figure 11:
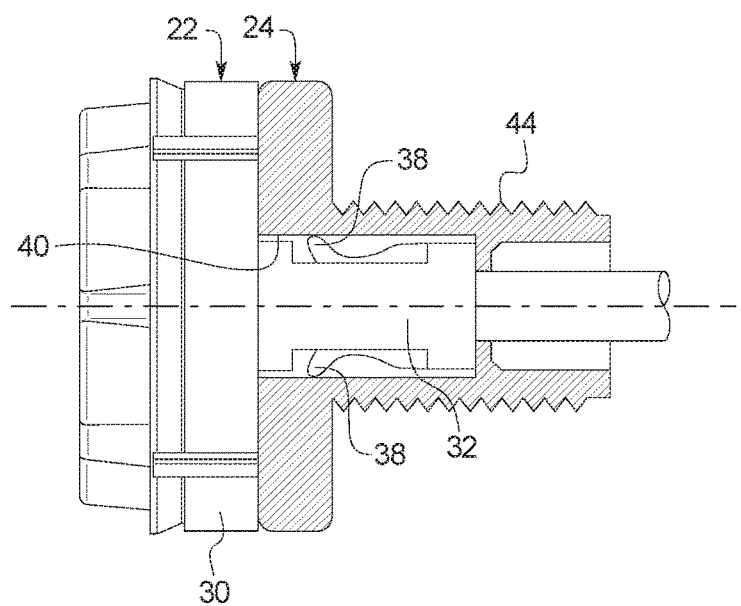
FIG. 11 is another side view of the stopper, the rod and the plunger similar to FIG. 10, but showing the plunger extending into a plunger receiving space defined within the stopper, the plunger receiving space being dimensioned to restricting movement the rod engaging clips such that the rod cannot be released from the plunger in accordance with the first embodiment.
Figure 12:
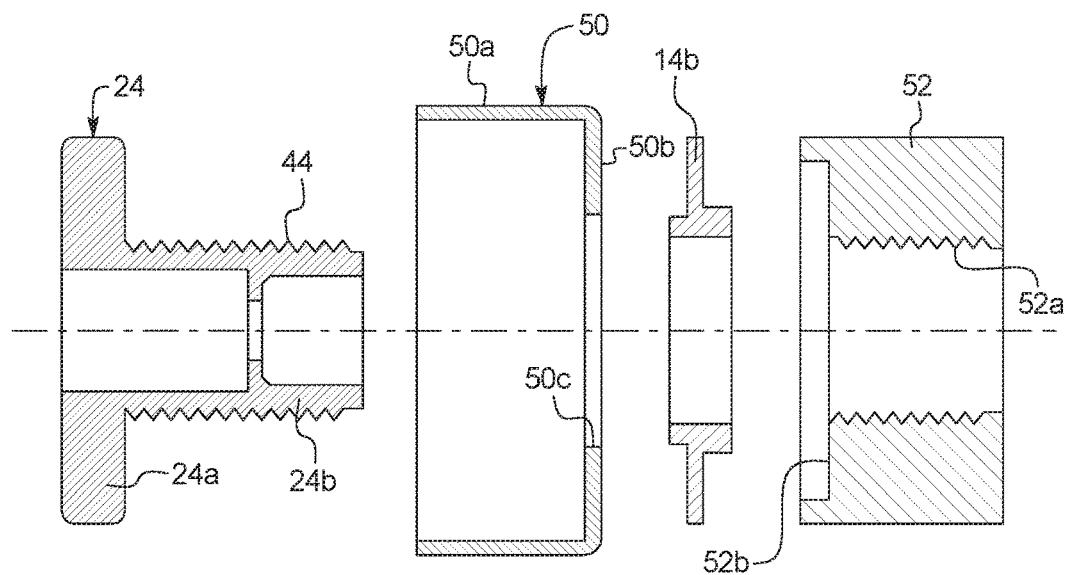
FIG. 12 is an exploded side cross-sectional view of the stopper, along with a stopper supporting end of the dispenser assembly, a cup-shaped member and a retainer just prior to assembly of the stopper to the stopper supporting end of the dispenser assembly in accordance with the first embodiment.

A description of the stopper 24 is now provided initially with reference to FIGS. 10, 11 and 12.

The stopper 24 is preferably a molded plastic element but can alternatively be machined or otherwise formed of a metallic material. The stopper 24 has a first section 24a and a second section 24b. The first section 24a has an overall disk shape and the second section 24b has a cylindrical shape. The first and second sections 24a and 24b are unitarily formed as a single monolithic element. The first section 24a has an outer diameter $D_5$ and the second section 24b has an outer diameter $D_6$ that is smaller than the outer diameter $D_5$. The stopper 24 defines a cylindrically shaped plunger receiving space 40 (hereinafter referred to as the plunger receiving space 40) with a first portion 40a and a second portion 40b separated by a wall 40c. An aperture 42 extends from the first portion 40a of the plunger receiving space 40 to the second portion 40b. The aperture 42 is dimensioned to receive the rod 20, which extends through the aperture 42 as shown in FIGS. 10 and 11.

As shown in FIG. 11, an outer surface of the second section 24b of the stopper 24 includes threads 44, whose purpose is described in greater detail below.

As shown in FIG. 10, the first portion 40a of the plunger receiving space 40 has an inner diameter $D_7$ that is dimensioned such that with the rod receiving structure 32 of the plunger 22 located within the plunger receiving space 40, movement of the rod engaging clips 38 is restricted by contact with surfaces of the plunger receiving space 40, thereby preventing release of the rod 20 from the plunger 22.

More specifically, the inner diameter $D_7$ of the first portion 40a of the plunger receiving space 40 is equal to or only slightly larger than the outer diameter $D_3$ of the rod engaging clips 38 with the rod engaging clips 38 being engaged with the rod 20 and fully installed to the plunger 22. Preferably, the outer diameter $D_3$ at the free ends 38a (distal ends) of the rod engaging clips 38 is approximately 95% or more of the diameter $D_7$ of the first portion 40a of the plunger receiving space 40 such that movement of the rod engaging clips 38 is restrained, with the rod engaging clip 38 being located within the plunger receiving space 40 of the stopper 24. Further, the diameter $D_7$ of the first portion 40a of the plunger receiving space 40 is significantly smaller than the outer diameter $D_4$ (FIG. 7) when the rod engaging clips 38 are spread apart from each other to install or release the rod 20 from the plunger 22, as shown in FIG. 7. Consequently, with the rod receiving structure 32 being within the plunger receiving space 40 of the stopper 24, the rod engaging clips 38 are confined and prevented from moving out of the clip receiving recess 28a of the rod 20. In other words, it is not possible to pull the rod 20 out of the plunger 22 when the rod receiving structure 32 is confined within the plunger receiving space 40 of the stopper 24, as shown in FIG. 11, without doing damage or destroying one or more of the rod 20, the plunger 22, the stopper 40.

However, when the rod receiving structure 32 is removed from the plunger receiving space 40 of the stopper 24, as shown in FIG. 10, movement of the rod engaging clips 38 is unrestricted, and hence it is possible to separate the rod 20 from the plunger 22 upon application of a predetermined force applied to the rod 20 and the plunger 22, pulling them apart from one another.

As shown in FIGS. 12-15, the stopper 24 can be removably attached to the stopper supporting end 14b (a rearward end) of dispenser assembly 10. Specifically, the stopper supporting end 14b can include two separate spaced apart projections as shown in FIGS. 12-15. The stopper 24 can be inserted between the projections of the stopper supporting end 14b, as shown in FIGS. 12-15. Alternatively, the stopper supporting end 14b can include an aperture with the second portion 24b inserted through the aperture.

Figure 13:
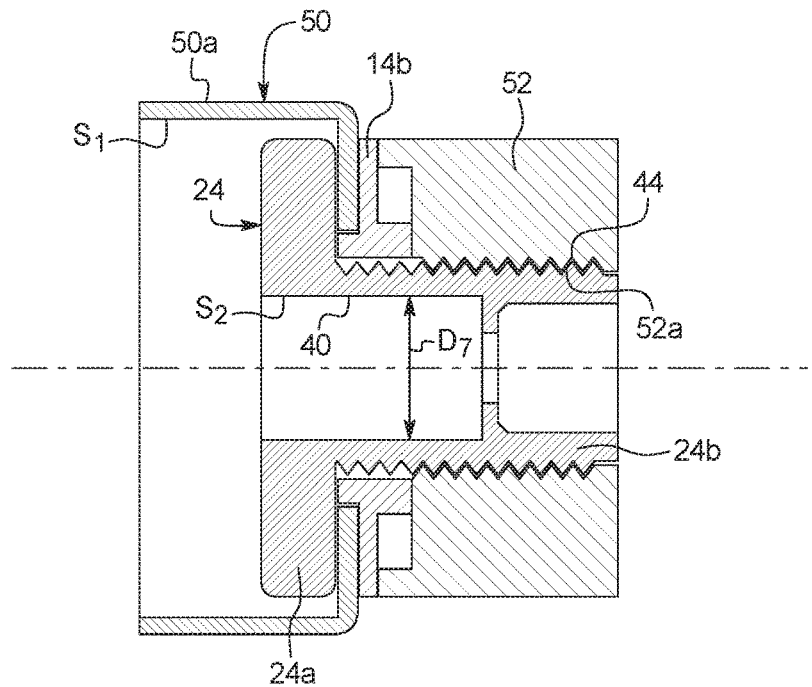
FIG. 13 is a side cross-sectional view of the stopper shown installed to the stopper supporting end of the dispenser assembly with the cup-shaped member being confined between the stopper and the stopper supporting end of the dispenser assembly via threaded tightening of the retainer to the stopper in accordance with the first embodiment.

A cup-shaped member 50 is fitted to the first section 24a of the stopper 24 and the stopper supporting end 14b. The cup-shaped member 50 includes an annular wall 50a and a flat wall 50b perpendicular to the annular wall 50a. The flat wall 50b includes a central aperture 50c. The second section 24b of the stopper 24 extends through the central aperture 50c. A retainer 52 has internal threads 52a that thread onto the threads 44 of the second section 24b, as shown in FIG. 13. With the retainer 52 fixed (threaded) to the threads 44 of the second section 24b of the stopper 24, the stopper supporting end 14b of the dispenser assembly 10 is held between the retainer 52 and the first section 24a of the stopper 24.

As shown in FIG. 13, the retainer 52 basically clamps the cup-shaped member 50 to the stopper 24. Consequently, the cup-shaped member 50 and the stopper 24 are rigidly fixed to one another once the retainer 52 is tightened to the second section 24b of the stopper 24. The annular wall 50a of the cup-shaped member 50 extends, or further defines the plunger receiving space 40. Consequently, the plunger receiving space 40 includes a first space $S_1$ and a second space $S_2$. The first space $S_1$ is defined by an inner surface of the annular wall 50a and the second space $S_2$ is defined by the inner surface of the space 40 of the first and second portions 24a and 24b of the stopper 24, as indicated in FIG. 13. The inner surface of the space 40 of the first and second portions 24a and 24b of the stopper 24 is concentric with the inner surface of the annular wall 50a of the cup-shaped member 50. As is clear in FIG. 13, the inner surface of the annular wall 50a defines an inner diameter that is more than twice the size of the diameter $D_7$ of the space 40 of the stopper 24.

Figure 14:
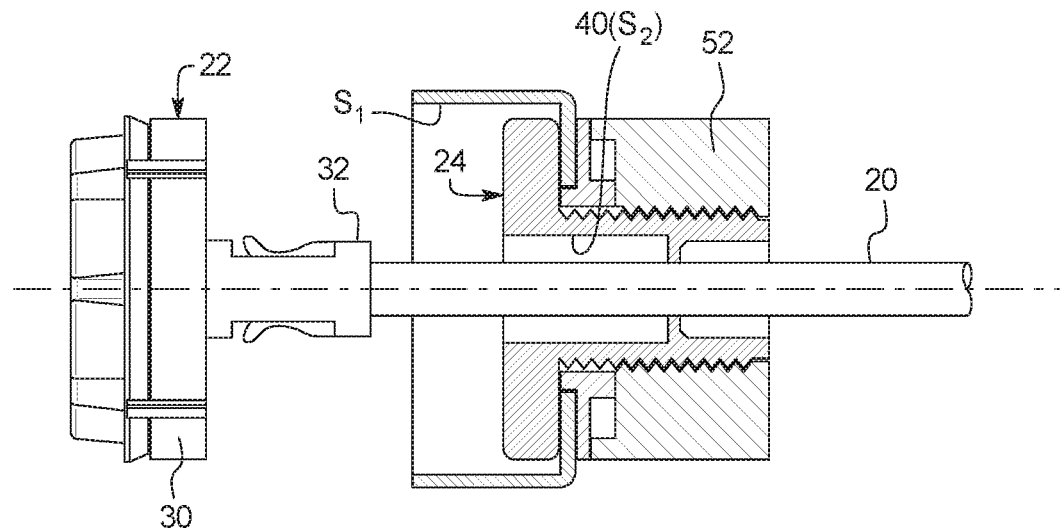
FIG. 14 is a side cross-sectional view of the stopper shown installed to the stopper supporting end of the dispenser assembly with the rod extending through the stopper and the plunger being spaced apart from the stopper in accordance with the first embodiment.
Figure 15:
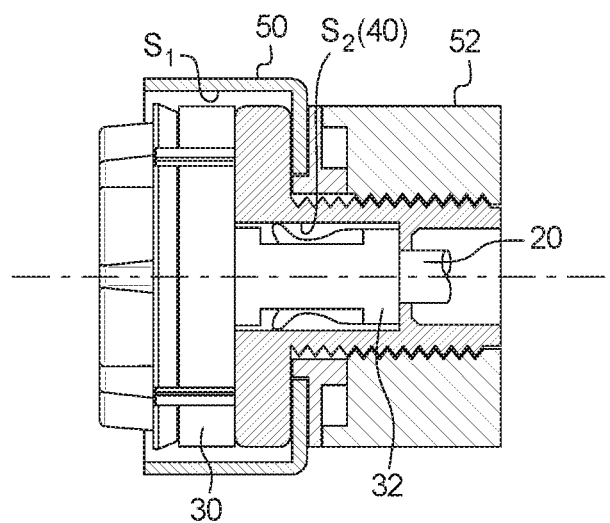
FIG. 15 is a side cross-sectional view of the stopper shown installed to the stopper supporting end of the dispenser assembly and showing the plunger extending into the plunger receiving space of the stopper restricting movement the rod engaging clips such that the rod cannot be released from the plunger in accordance with the first embodiment.

As shown in FIGS. 14 and 15, the plunger 22 is configured and dimensioned such that with the rod receiving structure 32 located within the second space $S_2$ of the plunger receiving space 40, the disk-shaped portion 30 of the plunger 22 is located within the first space $S_1$.

Figure 16:
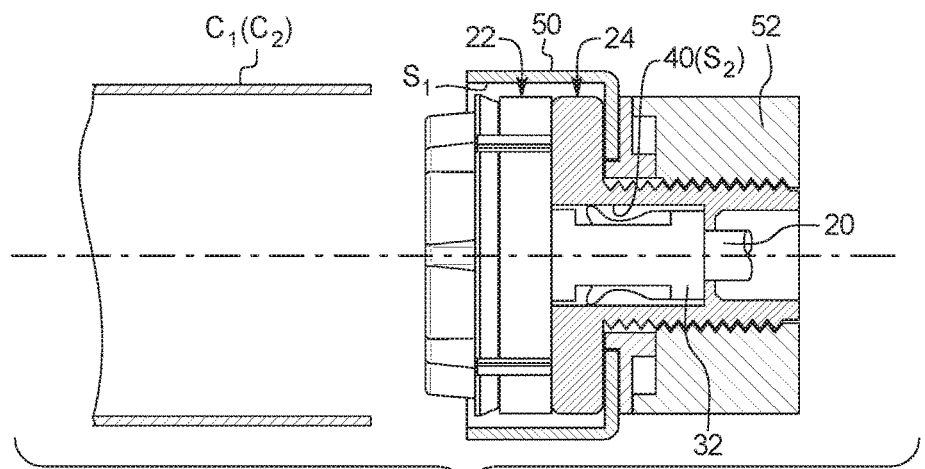
FIG. 16 is a side cross-sectional view of the stopper, the rod, the plunger and the stopper supporting end of the dispenser assembly showing a cartridge prior to installation to a cup-shaped member of the stopper in accordance with the first embodiment.
Figure 17:
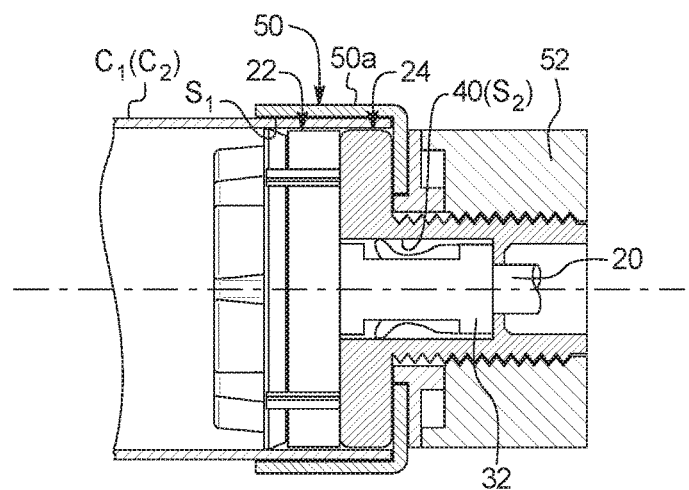
FIG. 17 is a side cross-sectional view of the stopper, the rod, the plunger and the stopper supporting end of the dispenser assembly showing the cartridge after installation to the cup-shaped member of the stopper in accordance with the first embodiment.
Figure 18:
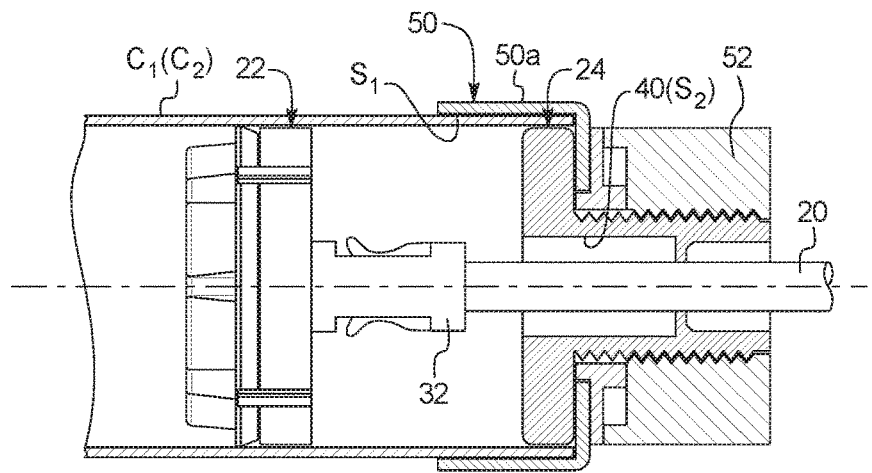
FIG. 18 is a side cross-sectional view of the stopper, the rod, the plunger and the stopper supporting end of the dispenser assembly showing the plunger (a piston) applying a dispensing force to contents of the cartridge such that the plunger is moved further into the cartridge in accordance with the first embodiment.
Figure 19:
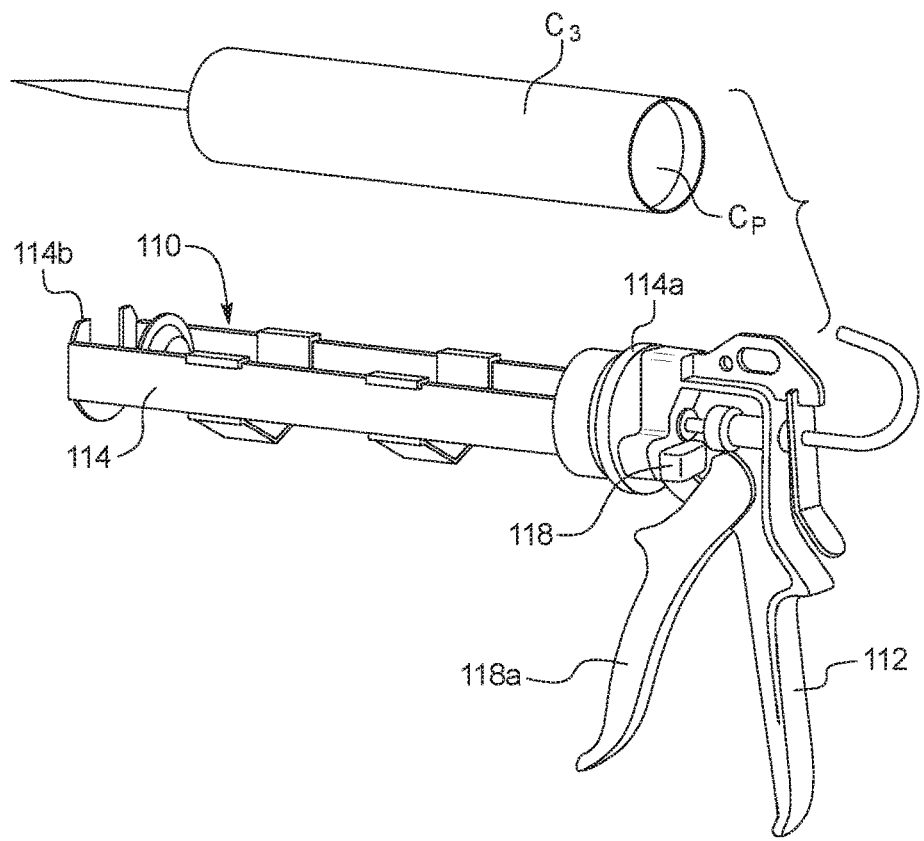
FIG. 19 is a perspective view of a dispenser assembly that includes a force applying rod with a plunger attached thereto, a stopper and a disposable cartridge with an internal piston in accordance with a second embodiment.
Figure 20:
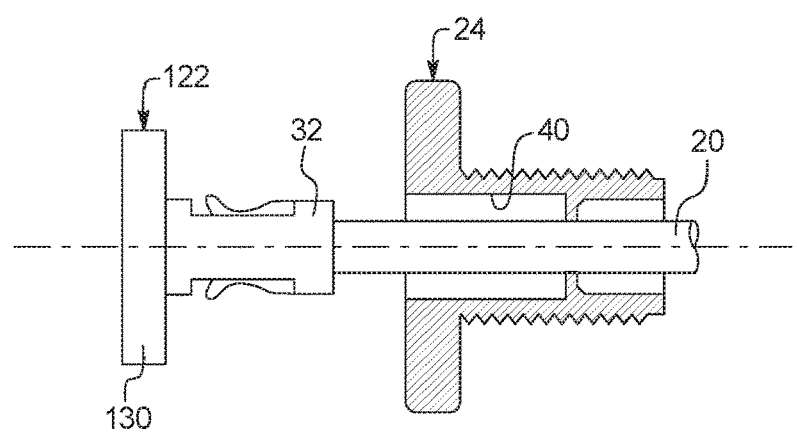
FIG. 20 is a side cross-sectional view of the stopper, the rod and the plunger in accordance with the second embodiment.
Figure 21:
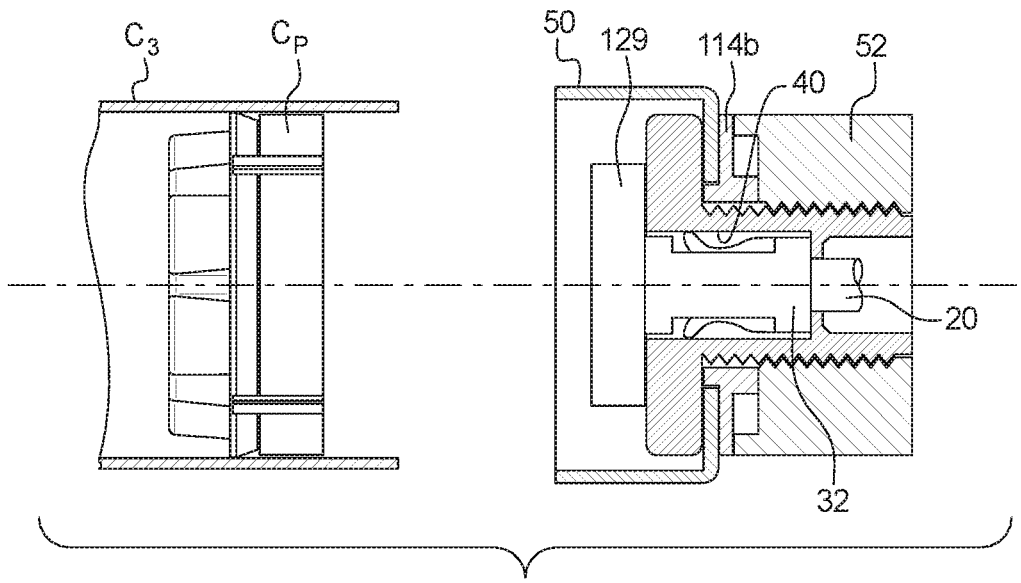
FIG. 21 is a side cross-sectional view of the stopper, the rod, the plunger and the stopper supporting end of the dispenser assembly showing the cartridge and its internal piston prior to installation to a cup-shaped member of the stopper in accordance with the second embodiment.
Figure 22:
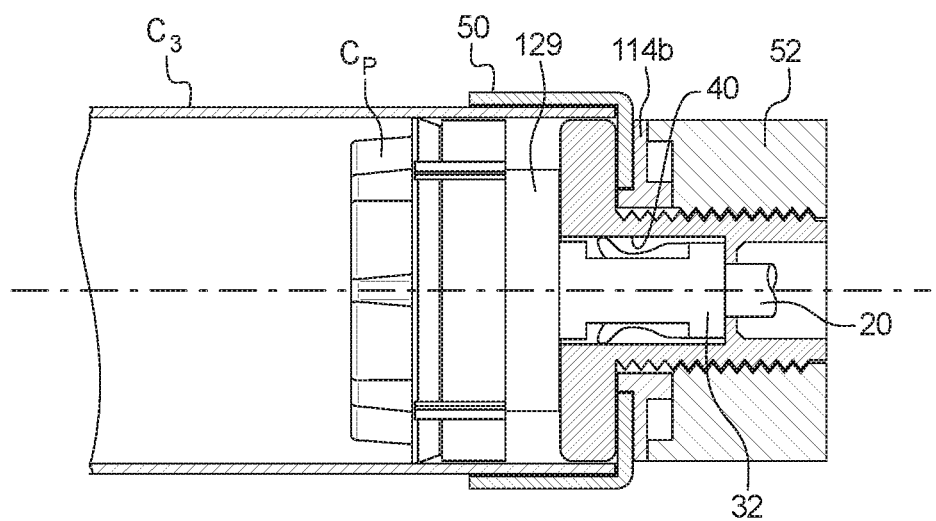
FIG. 22 is a side cross-sectional view of the stopper, the rod, the plunger and the stopper supporting end of the dispenser assembly showing the cartridge and its internal piston prior after installation to the cup-shaped member of the stopper in accordance with the second embodiment.

As shown in FIGS. 16-18, outer diameter of the cartridge $C_1$ is equal to or slightly smaller that the inner surface of the annular wall 50a. Consequently, the cartridge $C_1$ can be inserted into the cup-shaped member 50. Further, an inner diameter of the cartridge $C_1$ is approximately equal to the outer diameter of the disk-shaped portion 30 (piston) of the plunger 22. As force is applied to the disk-shaped portion 30 by the rod 20, the disk-shaped portion 30 can push against the contents of the cartridge $C_1$ thereby dispensing the contents of the cartridge $C_1$.

After the contents of the cartridge $C_1$ have been exhausted, the plunger 22 has typically been pushed well into the cartridge $C_1$. Consequently, it is necessary to apply a pulling or retracting force on the rod 20 in order to remove the plunger 22 from the cartridge $C_1$. The rod engaging clips 38 are designed, configured and dimensioned such that the force applied by the rod engaging clips 38 against the clip receiving recess 28a of the rod 20 is sufficient to grip the rod 20 during the retracting movement of the rod 20 and plunger 22 out of the cartridge $C_1$. In other words, the retracting force typically applied to the rod 20 to retract the plunger 22 out of the cartridge $C_1$ is typically insufficient to overcome the clamping forces applied by the rod engaging clips 38 to the rod 20. Consequently, retracting the rod 20 and plunger 22 out of the cartridge $C_1$ is easily accomplished. As the plunger 22 moves out of and possibly away from the cartridge $C_1$, the rod engaging clips 38 and the rod receiving structure 32 of the plunger 22 moves into the plunger receiving space 40 of the stopper 24. Therefore, if forces are applied to the rod 20 greater than and in the same direction as the retracting forces applied to the rod 20, the plunger receiving space 40 restricts movement of the rod engaging clips 38 preventing release of the plunger 22 from the rod 20.

The configurations of the rod 20 and the plunger 22 as described herein, prevent the plunger 22 from separating from the rod 20 during cartridge replacement procedures.

Second Embodiment

Referring now to FIGS. 19-22, a dispenser assembly 110 in accordance with a second embodiment will now be explained. In view of the similarity between the first and second embodiments, the parts of the second embodiment that are identical to the parts of the first embodiment will be given the same reference numerals as the parts of the first embodiment. Moreover, the descriptions of the parts of the second embodiment that are identical to the parts of the first embodiment may be omitted for the sake of brevity. The parts of the second embodiment that differ from the parts of the first embodiment will be indicated with a single prime (').

The dispenser assembly 110 includes a handle 112, a cartridge receiving structure 114, a material dispensing end 114a, a stopper supporting end 114b, a replaceable (disposable) cartridge $C_3$, a dispensing mechanism 118 with a trigger 118a and a plunger 122. The dispenser assembly 110 also includes the rod 20 and the stopper 24, as described above with respect to the first embodiment.

In the second embodiment, the cartridge $C_3$ includes its own piston $C_P$. Further, the plunger 122 includes a disk-shaped portion 130 and the rod receiving structure 32 (as described above with respect to the first embodiment).

In the second embodiment, the disk-shaped portion 130 is not a piston, but rather is a disk-shaped plate that is configured to contact and selectively apply dispensing force to the piston $C_P$ of the cartridge $C_3$.

Third Embodiment

Figure 23:
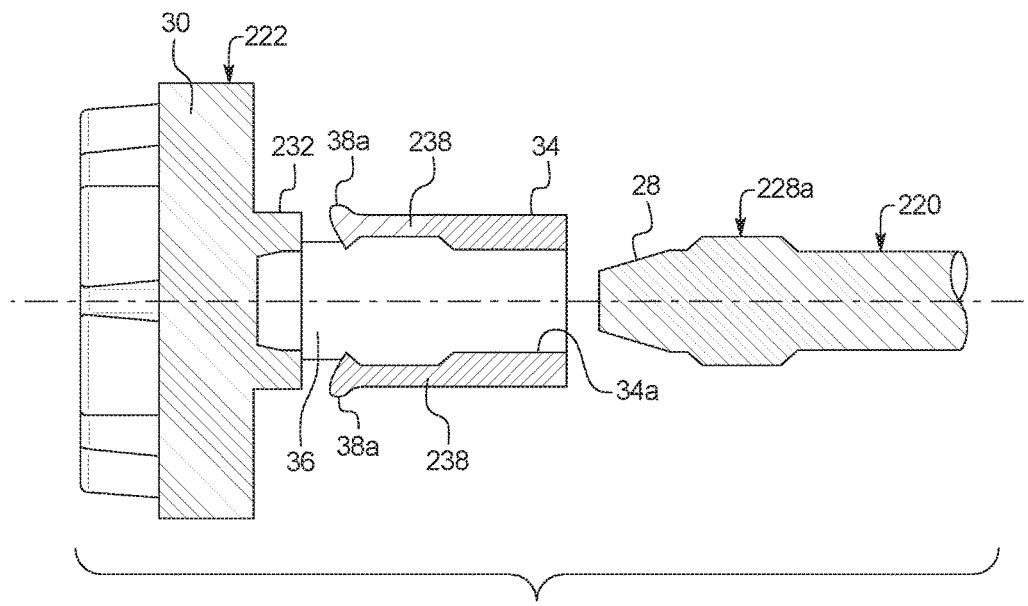
FIG. 23 is an exploded side cross-sectional view of a rod and a plunger shown just prior to attachment of the rod to the plunger in accordance with a third embodiment.
Figure 24:
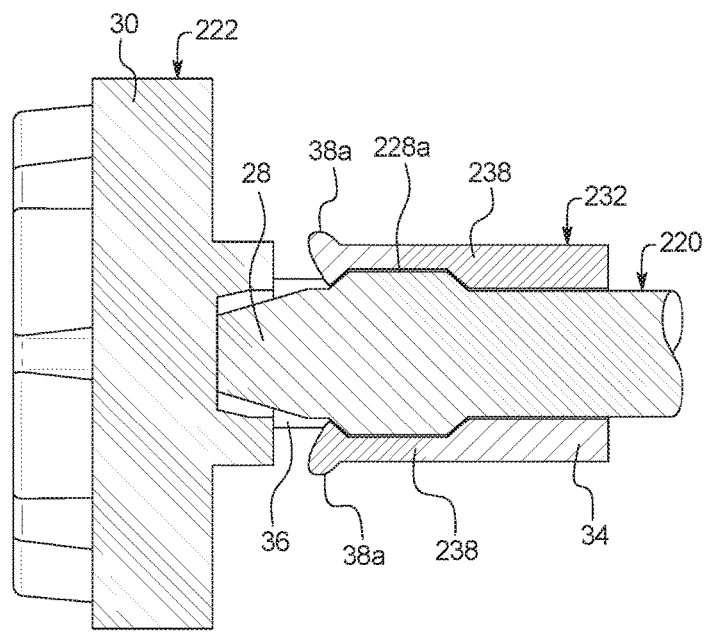
FIG. 24 is another side cross-sectional view of the rod and the plunger similar to FIG. 23 showing the rod fully inserted into the plunger with the two rod engaging clips contacting projection formed on the rod, retaining the plunger on the rod in accordance with the third embodiment.
Figure 25:
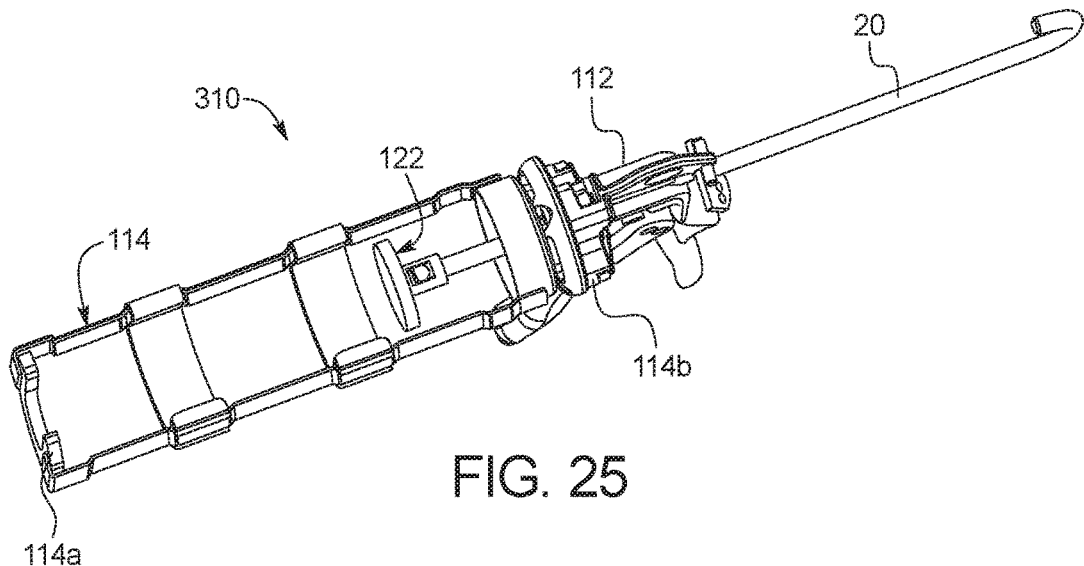
FIG. 25 is a top view of a dispenser assembly that includes a force applying rod with a plunger attached thereto, a stopper and a structure configured to receive a disposable cartridge in accordance with a fourth embodiment.
Figure 26:
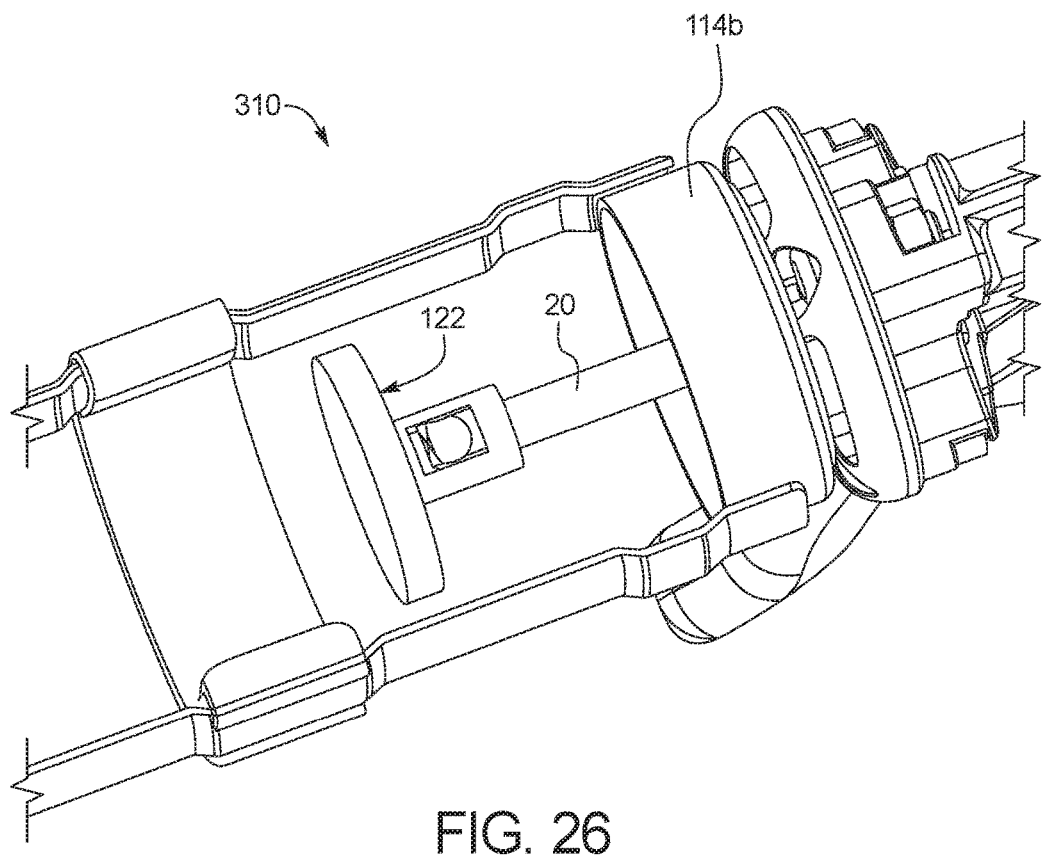
FIG. 26 is another top view of a portion of the dispenser assembly depicted in FIG. 25 showing details of the force applying rod and the plunger attached thereto in accordance with the fourth embodiment.

Referring now to FIGS. 23-24, a rod 220 and plunger 222 in accordance with a third embodiment will now be explained. In view of the similarity between the first and third embodiments, the parts of the third embodiment that are identical to the parts of the first embodiment will be given the same reference numerals as the parts of the first embodiment. Moreover, the descriptions of the parts of the third embodiment that are identical to the parts of the first embodiment may be omitted for the sake of brevity.

In the third embodiment, the rod 220 replaces the rod 20 of the first embodiment and can be used in the dispenser 10 in a manner consistent with the use of the rod 20. The rod 220 is identical to the rod 20 of the first embodiment, except that the clip receiving recess 28a of the first embodiment is replaced with a clip receiving protrusion 228a (a clip receiving portion). The clip receiving protrusion 228a is an annular protrusion (encircling the rod 220) that has an outer diameter that is greater than the outer diameter of the remainder of the rod 220.

The plunger 222 replaces the plunger 22 of the first embodiment and can be used in the dispenser 10 in a manner consistent with the use of the plunger 22. The plunger 222 has the disk-shaped portion 30 as described with respect to the first embodiment, and, also includes a rod receiving structure 232. The rod receiving structure 232 includes the annular end ring 34 and the support portions 36, as described above with reference to the first embodiment. However, in the third embodiment, the rod engaging clips 38 are replaced with modified rod engaging clips 238. The rod engaging clips 238 are similar to the rod engaging clips 38 of the first embodiment, except that the rod engaging clips 238 are dimensioned to engage the clip receiving protrusion 228a, as shown in FIG. 24. The rod engaging clips 238 include the free ends 38a as described above with respect to the first embodiment. Further, the free ends 38a of the rod engaging clips 238 interact with the plunger receiving space 40 of the stopper 24 (not shown in FIGS. 23 and 24), in exactly the same manner as the free ends 38a of the rod engaging clips 38 of the first embodiment. Specifically, with the rod receiving structure 232 is located within the plunger receiving space 40 of the stopper 24, the rod 220 is difficult, if not impossible to remove from the rod engaging clips 238 since the inner diameter of the plunger receiving space 40 of the stopper 24 prevents movement of the rod engaging clips 238.

Fourth Embodiment

Referring now to FIGS. 25-31, dispenser 310 in accordance with a fourth embodiment will now be explained. In view of the similarity between the first and fourth embodiments, the parts of the fourth embodiment that are identical to the parts of the first embodiment will be given the same reference numerals as the parts of the first embodiment. Moreover, the descriptions of the parts of the fourth embodiment that are identical to the parts of the first embodiment may be omitted for the sake of brevity.

The dispenser assembly 310 is basically the same as the dispenser assembly 110 of the second embodiment with a few modifications as described below. Those parts of the dispenser assembly 310 that are the same as the dispenser assembly 110 of the second embodiment, are given the same reference numbers as the parts of the second embodiment.

The dispenser assembly 310 includes the handle 112, the cartridge receiving structure 114, the material dispensing end 114a, a stopper supporting end 114b, the dispensing mechanism 118 with the trigger 118a, and the plunger 122, as described above with respect to the second embodiment. The dispenser assembly 310 also includes the rod 20, as described above with respect to the first embodiment. However, in the fourth embodiment, the stopper 24 of the first and second embodiments is replaced with a stopper 324 that has been modified relative to the stopper 24 of the first and second embodiments.

In the fourth embodiment, the cartridge $C_3$ (not shown) includes its own piston (not shown). Further, the plunger 122 includes the disk-shaped portion 130 and the rod receiving structure 32 (as described above with respect to the first and second embodiments). Specifically, the rod receiving structure 32 includes the annular end ring 34 and the rod engaging clips 38.

In the fourth embodiment, the disk-shaped portion 130 is not a piston, but rather is a disk-shaped plate that is configured to contact and selectively apply dispensing force to the piston (not shown) of the cartridge $C_3$ (not shown).

Figure 27:
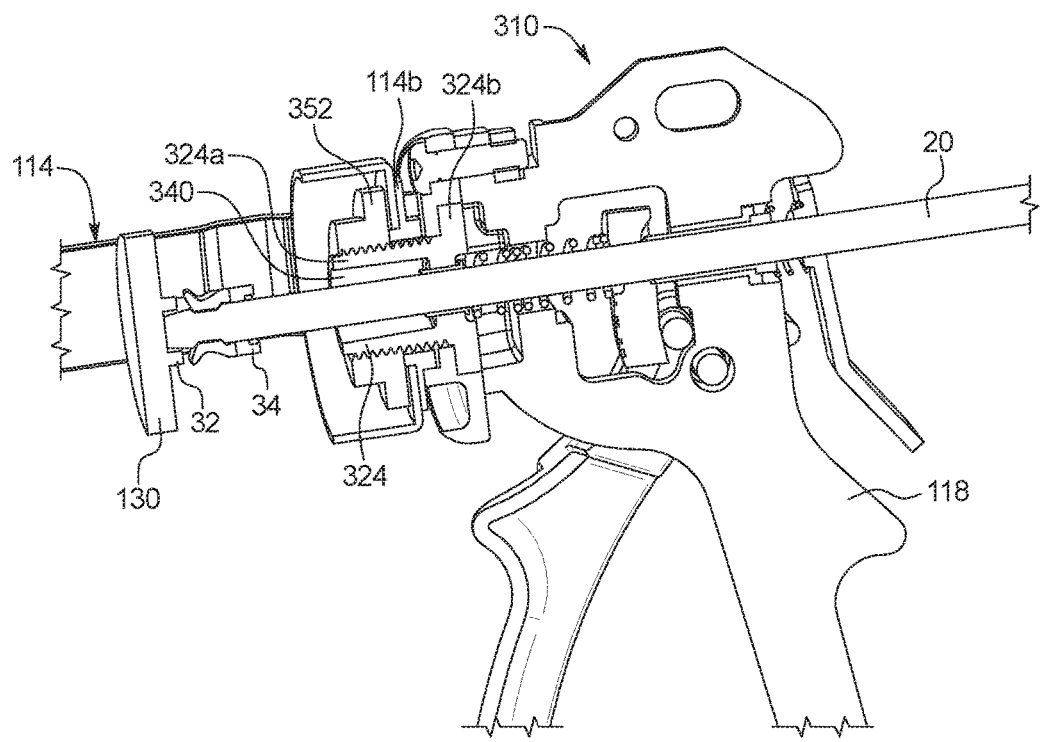
FIG. 27 is a side cross-sectional view of the portion of the dispenser depicted in FIG. 26 showing further details of the force applying rod, the plunger attached thereto and a stopper attached to the dispenser, with the plunger moved away from the stopper in accordance with the fourth embodiment.
Figure 28:
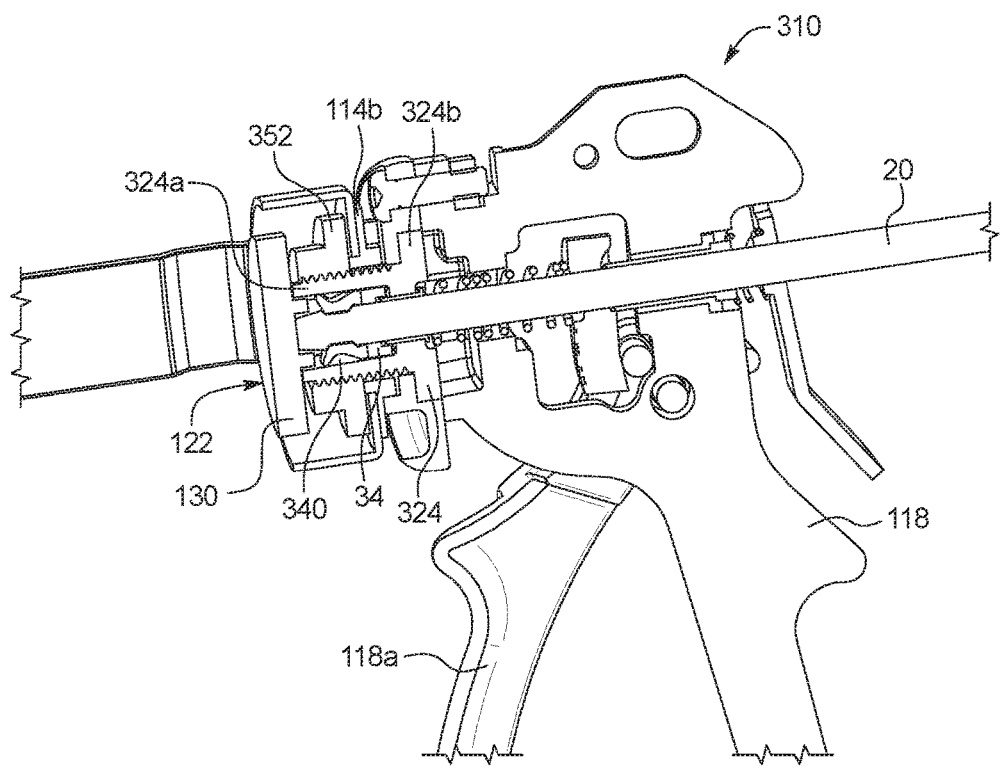
FIG. 28 is another side cross-sectional view of the portion of the dispenser similar to FIG. 27 showing further details of the force applying rod, the plunger and the stopper, with the plunger moved into a plunger receiving space of the stopper restricting movement of clips of the plunger thereby preventing the rod from being removed from the plunger in accordance with the fourth embodiment.
Figure 29:
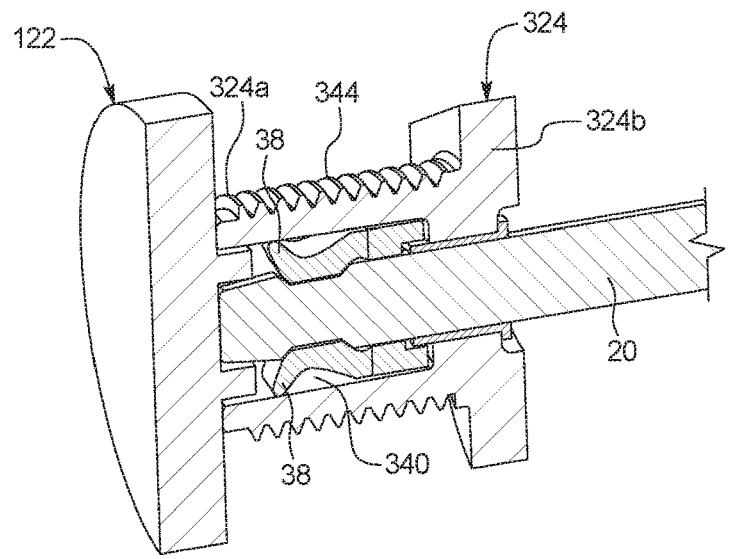
FIG. 29 is another side cross-sectional view of the portion of the dispenser showing further details of the force applying rod, the plunger and the stopper, with the plunger moved into a plunger receiving space of the stopper restricting movement of clips of the plunger thereby preventing the rod from being removed from the plunger in accordance with the fourth embodiment.

In the fourth embodiment, the stopper 24 of the first and second embodiments is replaced with a modified stopper 324. The stopper 324 includes a first section 324a and a second section 324b. The first section 324a has threads formed on an outer periphery that engage internal threads of a retainer 352 (FIGS. 27 and 28). The second section 324b has a disk shape and when the stopper 324 is installed to the stopper supporting end 114b of the dispenser assembly 310, the second section 324b is installed at a rearward side of the dispenser assembly 310 outside of the cartridge receiving structure 114. The first section 324a has a cylindric shape and extends through an opening or gap in the stopper supporting end 114b into cartridge receiving space of the cartridge receiving structure 114. The retainer 352 secures the stopper 324 in place.

Figure 30:
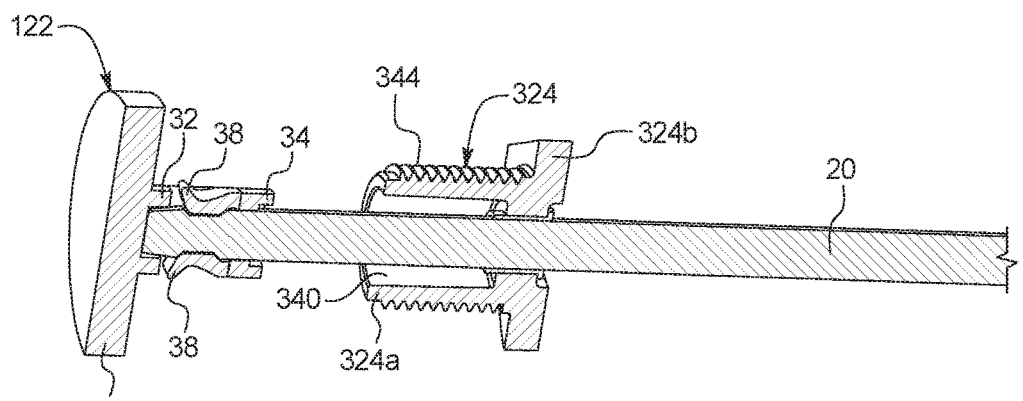
FIG. 30 is a side schematic view of the rod, the plunger and the stopper with the stopper moved away from the plunger in accordance with the fourth embodiment.
Figure 31:
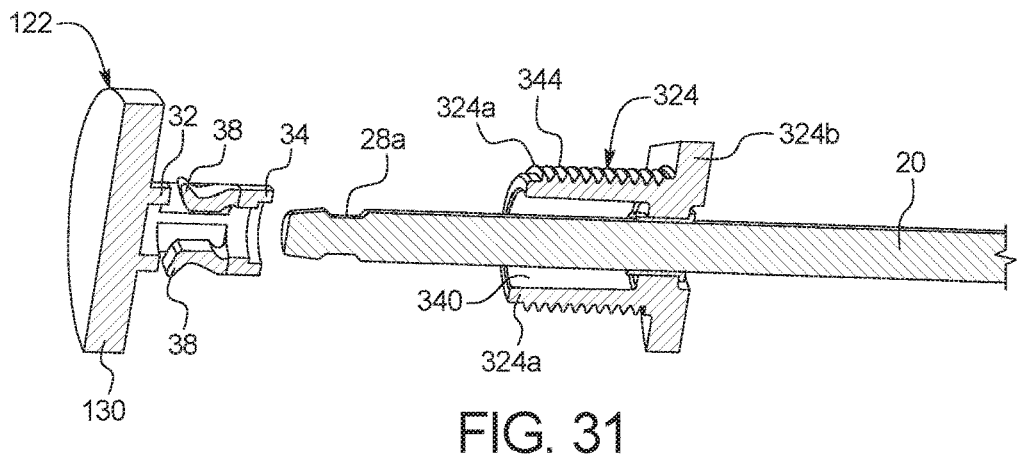
FIG. 31 is another side schematic view of the rod, the plunger and the stopper with the plunger separated from the rod in accordance with the fourth embodiment.

The first section 324a of the stopper 324 defines a plunger receiving space 340 that is dimensioned in a manner identical to the plunger receiving space 40 of the first and second embodiments, such that when the rod receiving structure 32, and in particular, the rod engaging clips 38, are located within the plunger receiving space 340, movement of the rod engaging clips 38 is restricted, thereby preventing the release of the rod 20 from the rod receiving structure 32. As shown in FIGS. 30 and 31, once the rod receiving structure 32, and in particular, the rod engaging clips 38, are moved out of the plunger receiving space 340, movement of the rod engaging clips 38 is only restricted by the resilient elastic forces of the rod engaging clips 38, and with sufficient force applied to the plunger 324 and the rod 20, the rod 20 from the rod receiving structure 32 can be separated, if desired.

The various elements of the dispenser assemblies 10 and 110 (other than the rods 20 and 220, the plungers 22, 122 and 222, and the stoppers 24 and 324), are conventional components that are well known in the art. Since such dispenser assembly elements are well known in the art, these structures will not be discussed or illustrated in detail herein. Rather, it will be apparent to those skilled in the art from this disclosure that the components can be any type of structure that can be used to carry out the present invention.

General Interpretation of Terms

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Also as used herein to describe the above embodiments, the following directional terms "forward", "rearward", "above", "downward", "vertical", "horizontal", "below" and "transverse" as well as any other similar directional terms refer to those directions of the dispenser assembly. Accordingly, these terms, as utilized to describe the present invention should be interpreted relative to the dispenser assembly.

The term "configured" as used herein to describe a component, section or part of a device that includes structure that is constructed to carry out the desired function.

The terms of degree such as "substantially", "about" and "approximately" as used herein mean a reasonable amount of deviation of the modified term such that the end result is not significantly changed.

While only selected embodiments have been chosen to illustrate the present invention, it will be apparent to those skilled in the art from this disclosure that various changes and modifications can be made herein without departing from the scope of the invention as defined in the appended claims. For example, the size, shape, location or orientation of the various components can be changed as needed and/or desired. Components that are shown directly connected or contacting each other can have intermediate structures disposed between them. The functions of one element can be performed by two, and vice versa. The structures and functions of one embodiment can be adopted in another embodiment. It is not necessary for all advantages to be present in a particular embodiment at the same time. Every feature which is unique from the prior art, alone or in combination with other features, also should be considered a separate description of further inventions by the applicant, including the structural and/or functional concepts embodied by such features. Thus, the foregoing descriptions of the embodiments according to the present invention are provided for illustration only, and not for the purpose of limiting the invention as defined by the appended claims and their equivalents.

What is claimed is:

1. A dispenser assembly, comprising:
a rod having a plunger receiving end with a clip receiving portion;
a plunger having a rod receiving structure with a rod engaging clip biased to fit to the clip receiving portion of the rod for movement therewith; and
a stopper having a plunger receiving space that defines an aperture extending through the plunger receiving space with the rod extending through the aperture, the plunger receiving space being dimensioned such that with the rod receiving structure of the plunger located within the plunger receiving space, movement of the rod engaging clip is restricted by contact with surfaces of the plunger receiving space preventing release of the rod from the plunger, and, the stopper being further configured such that with the rod receiving structure being spaced apart from the plunger receiving space, movement of the rod engaging clip is unrestricted.

2. The dispenser assembly according to claim 1, wherein the clip receiving portion is an annular recess formed on the rod.

3. The dispenser assembly according to claim 1, wherein the clip receiving portion is an annular projection formed on the rod.

4. The dispenser assembly according to claim 1, wherein the rod receiving structure has an overall cylindrical shape and the clip receiving portion has an annular shape, and the rod engaging clip of the rod receiving structure of the plunger includes a plurality of rod engaging clips circumferentially spaced apart from one another.

5. The dispenser assembly according to claim 1, wherein the plunger receiving space of the stopper includes a first space and a second space, the first space being defined by a first inner surface of a first annular wall and the second space being defined by a second inner surface of a second annular wall that is concentric with the first annular wall, the first and second annular walls being rigidly connected to one another.

6. The dispenser assembly according to claim 5, wherein the first inner surface has a first diameter and the second inner surface with a second diameter that is smaller than the first diameter.

7. The dispenser assembly according to claim 6, wherein the plunger is configured and dimensioned such that with the rod receiving structure located within the second space of the plunger receiving space, a disk-shaped portion of the plunger is located within the first space of the plunger receiving space.

8. The dispenser assembly according to claim 1, wherein the plunger includes a disk-shaped portion that is dimensioned and configured to contact a piston within a disposable material filled cartridge.

9. The dispenser assembly according to claim 1, wherein the plunger includes a disk-shaped portion that is a piston dimensioned and configured to directly press against material within a disposable material filled cartridge.

10. The dispenser assembly according to claim 1, further comprising:
a handle assembly having a cartridge receiving structure that includes a material dispensing end and a stopper supporting end with the stopper being attached to the stopper supporting end.

11. The dispenser assembly according to claim 10, wherein
the handle assembly includes a second cartridge receiving structure that extends parallel to the cartridge receiving structure, the second cartridge receiving structure, and a dispensing nozzle having a mixing portion in which contents of a first cartridge installed to the cartridge receiving structure and contents of a second cartridge installed to the second cartridge structure are mixed prior to being dispensed through the dispensing nozzle.

12. The dispenser assembly according to claim 11, wherein
the handle assembly further includes:
a second rod having a second plunger receiving end with a second clip receiving portion, the second rod being supported for movement along the second cartridge receiving structure;
a second plunger having a second rod receiving structure with a second rod engaging clip that is biased to fit to the second clip receiving portion of the second rod for movement therewith; and
a second stopper supported to a rearward end of the second cartridge receiving structure, the second rod extending movably through an aperture of the second stopper, the second stopper having a second plunger receiving space that is dimensioned such that with the second rod receiving structure located within the second plunger receiving space, movement of the second rod engaging clip is restricted by contact with surfaces of the second plunger receiving space preventing release of the second rod from the second plunger.

13. The dispenser assembly according to claim 10, wherein
the handle assembly further includes a rod advancing mechanism configured to move the rod thereby causing the plunger to apply pressure to a removable cartridge installed to the cartridge receiving structure in order to dispense contents of the removable cartridge.

14. A dispenser assembly, comprising:
a handle assembly having a cartridge receiving structure that includes a material dispensing end and a stopper supporting end;
a rod having a plunger receiving end with a clip receiving portion;
a plunger having a rod receiving structure with a rod engaging clip biased to fit to the clip receiving portion of the rod for movement therewith; and
a stopper attached to the stopper supporting end, the stopper having a plunger receiving space that defines an aperture extending through the plunger receiving space with the rod extending through the aperture, the plunger receiving space being dimensioned such that with the rod receiving structure of the plunger located within the plunger receiving space, movement of the rod engaging clip is restricted by contact with surfaces of the plunger receiving space preventing release of the rod from the plunger, and the stopper is further configured such that with the rod receiving structure being spaced apart from the plunger receiving space, movement of the rod engaging clip is unrestricted.

15. The dispenser assembly according to claim 14, wherein
the clip receiving portion is an annular recess formed on the rod, and
the rod engaging clip of the rod receiving structure of the plunger includes a plurality of rod engaging clips circumferentially spaced apart from one another.

16. The dispenser assembly according to claim 14, wherein
the plunger receiving space of the stopper includes a first space and a second space, the first space being defined by a first inner surface of a first annular wall and the second space being defined by a second inner surface of a second annular wall that is concentric with the first annular wall, the first and second annular walls being rigidly connected to one another, and the first inner surface has a first diameter and the second inner surface with a second diameter that is smaller than the first diameter, wherein
the rod receiving structure and a distal end of the rod engaging clip define a third diameter that is approximately 95% of the second diameter such that movement of the rod engaging clip is restrained with the rod engaging clip being located within the second space.

17. The dispenser assembly according to claim 16, wherein
the plunger is configured and dimensioned such that with the rod receiving structure located within the second space of the plunger receiving space, a disk-shaped portion of the plunger is located within the first space of the plunger receiving space, and
the disk-shaped portion is dimensioned and configured to contact a piston within a disposable material filled cartridge.

18. The dispenser assembly according to claim 16,
wherein the plunger is configured and dimensioned such that with the rod receiving structure located within the second space of the plunger receiving space, a disk-shaped portion of the plunger is located within the first space of the plunger receiving space, and
the disk-shaped portion is a piston dimensioned and configured to directly press against material within a disposable material filled cartridge.

19. The dispenser assembly according to claim 14, wherein
the clip receiving portion is an annular projection formed on the rod.

* * * * *